United States Patent
Dudala

(10) Patent No.: US 9,058,352 B2
(45) Date of Patent: Jun. 16, 2015

(54) SYSTEM FOR DYNAMICALLY AND QUICKLY GENERATING A REPORT AND REQUEST FOR QUOTATION

(75) Inventor: Sharath Chandra Dudala, Malvern, PA (US)

(73) Assignee: Cerner Innovation, Inc., Kansas City, KS (US)

( * ) Notice: Subject to any disclaimer, the term of this patent is extended or adjusted under 35 U.S.C. 154(b) by 242 days.

(21) Appl. No.: 13/480,511

(22) Filed: May 25, 2012

(65) Prior Publication Data

US 2013/0080414 A1 Mar. 28, 2013

Related U.S. Application Data

(60) Provisional application No. 61/537,643, filed on Sep. 22, 2011.

(51) Int. Cl.
*G06F 17/30* (2006.01)
*G06F 19/00* (2011.01)

(52) U.S. Cl.
CPC ........ *G06F 17/30398* (2013.01); *G06F 19/327* (2013.01); *G06F 19/3487* (2013.01)

(58) Field of Classification Search
CPC .................. G06F 17/30386; G06F 17/30389; G06F 17/30398; G06F 17/30572; G06F 17/30651
USPC .................. 707/802, 803, 805, 807; 705/2, 3; 715/221, 22, 243
See application file for complete search history.

(56) References Cited

U.S. PATENT DOCUMENTS

| | | | |
|---|---|---|---|
| 4,553,261 A | 11/1985 | Froessl | |
| 4,945,476 A | 7/1990 | Bodick et al. | |
| 5,159,667 A | 10/1992 | Borrey | |
| 5,164,899 A | 11/1992 | Inn et al. | |
| 5,619,592 A | 4/1997 | Bloomberg | |

(Continued)

FOREIGN PATENT DOCUMENTS

| | | |
|---|---|---|
| EP | 0 544 432 A2 | 6/1993 |
| WO | 02/07091 A2 | 1/2002 |

OTHER PUBLICATIONS

"13 Objects, Images, and Applets", printed from website http://www.w3.org/TR/html4/struct/objects.html, printed Aug. 25, 2006.

(Continued)

*Primary Examiner* — Hares Jami
(74) *Attorney, Agent, or Firm* — Shook, Hardy & Bacon L.L.P.

(57) ABSTRACT

A system generates a request for quotation for a healthcare information system function using a stored template quotation format and multiple different quotation related data fields associated with multiple different healthcare information system elements. A search engine receives user entered text data associated with a desired healthcare information system element and searches stored information to identify multiple different quotation related data fields associated with a healthcare information system element in response to the entered text data. A quotation generator generates a display image showing items representing the identified multiple different quotation related data fields enabling a user to populate a template executable application image window with one or more of the identified data fields and initiate obtaining a quotation for providing the image window.

16 Claims, 10 Drawing Sheets

(56) References Cited

U.S. PATENT DOCUMENTS

| | | | |
|---|---|---|---|
| 5,647,021 | A | 7/1997 | Fortune et al. |
| 5,664,109 | A | 9/1997 | Czmpbell et al. |
| 5,832,450 | A | 11/1998 | Culp et al. |
| 5,924,074 | A | 7/1999 | Evans |
| 6,052,693 | A | 4/2000 | Hayward-Shott et al. |
| 6,084,585 | A | 7/2000 | Kraft et al. |
| 6,266,682 | B1 | 7/2001 | Lamarca |
| 6,341,287 | B1 | 1/2002 | Sziklai et al. |
| 6,668,253 | B1 | 12/2003 | Thompson et al. |
| 7,933,815 | B2 | 4/2011 | Hutty et al. |
| 7,979,456 | B2* | 7/2011 | Dettinger et al. ............ 707/765 |
| 2002/0082865 | A1 | 6/2002 | Bianco et al. |
| 2002/0103673 | A1 | 8/2002 | Atwood |
| 2003/0078806 | A1 | 4/2003 | Kudryk et al. |
| 2003/0208381 | A1 | 11/2003 | Walter et al. |
| 2004/0008223 | A1 | 1/2004 | Britton et al. |
| 2004/0220829 | A1 | 11/2004 | Baharav et al. |
| 2004/0254816 | A1 | 12/2004 | Myers |
| 2007/0078885 | A1* | 4/2007 | Klein, Jr. ..................... 707/102 |
| 2008/0016101 | A1* | 1/2008 | Ginsburg et al. ............. 707/102 |
| 2008/0103869 | A1 | 5/2008 | Hutty et al. |
| 2009/0125387 | A1 | 5/2009 | Mak et al. |
| 2009/0210256 | A1* | 8/2009 | Upadhyayula et al. ........... 705/4 |
| 2010/0008553 | A1* | 1/2010 | Holmstrom .................. 382/128 |
| 2011/0296298 | A1* | 12/2011 | Ahuja et al. .................. 715/248 |

OTHER PUBLICATIONS

Ted Padova, "PDF In-Depth, Acrobat PDF Forms: A Step-by-step Introduction", Feb. 1, 2001, web site http://www.planetpdf.com/developer/article.asp?ContentID=6480&mp (33 pages), printed on Nov. 23, 2005.

"W3C, HTML 4.01 Specification, W3C Recommendation Dec. 24, 1999", website: http://www.w3.org/TR/html4/, printed Nov. 23, 2005.

* cited by examiner

US 9,058,352 B2

SYSTEM FOR DYNAMICALLY AND QUICKLY GENERATING A REPORT AND REQUEST FOR QUOTATION

This is a non-provisional application of provisional application Ser. No. 61/537,643 filed Sep. 22, 2011, by S. C. Dudala.

FIELD OF THE INVENTION

This invention concerns a system for generating a request for quotation for healthcare information system resources from a vendor by populating a template quotation request with different quotation related data fields associated with a healthcare information system resource in response to a context sensitive search.

BACKGROUND OF THE INVENTION

The preparation of system specification documents and requests for quotation for acquiring a healthcare information system and related computer systems is a burdensome and protracted process. A request for work and resources often requires assistance from vendor company consultants. Doctors and Nurses tend to feel that a specification documents is too technical or complex in nature for them to understand and are reluctant to spend hours filling out complicated specification documents to request a quotation from a vendor. A user typically needs assistance in preparing a quotation request and is expected to have sufficient technical knowledge to fill out system and software specification documents. An incomplete or incorrectly filled specification document needs follow up by both vendor and requesting parties to clarify questions which is time consuming and costly. A system according to invention principles facilitates and accelerates preparation of reports and RFQs (requests for quotation) and addresses these problems.

SUMMARY OF THE INVENTION

A report-generation system dynamically generates a report on the fly and sends it to an HIS (Healthcare Information System) vendor for a quote and is customizable for various healthcare information systems (including Financial, Critical Care, Scheduling and order entry systems, for example). A system generates a request for quotation for healthcare information system resources from a vendor. At least one repository of information includes, a template quotation format and multiple different quotation related data fields associated with multiple different healthcare information system elements. A context sensitive search engine receives user entered text data associated with a desired healthcare information system element and searches the repository to identify multiple different quotation related data fields associated with a healthcare information system element in response to the entered text data. A quotation generator generates a display image showing items representing the identified multiple different quotation related data fields enabling a user to populate a template executable application image window with one or more of the identified data fields and submit the image window to obtain a quotation for providing the image window and associated executable application function.

DETAILED DESCRIPTION OF THE INVENTION

A system in one embodiment comprises a Table based Report-generation system that facilitates non-technical personnel in dynamically generating a report comprising a request for quotation for a healthcare information system, application, addition or function. The system generates a request for quotation on the fly and sends it to an HIS (Healthcare Information System) vendor for quotation. The system enables requesting quotations with a reduced number of user interactions (e.g. mouse clicks) advantageously supporting generation of an increased number of requests by customers. Further, since a high proportion (e.g., 90%) of quotations in some fields is converted to actual orders, this boosts vendor revenues. The system may be customized for various products (such as Financial, Critical Care, Scheduling, and Order Entry applications, for example).

The system facilitates non-technical customers in creating a draft (mockup) report comprising a request for quotation either from an existing model request for quotation (by adding or deleting fields) or in creating a new report in a reduced time period. A search field helps a user find different data fields from a database that the user requires in a request for quotation. In response to finding desired data fields, a user is able to drag and drop them on the request for quotation report creating a mock-up. Once the user is satisfied with the request for quotation layout, it may be communicated to a vendor for a quotation via activation of a button. The system helps customers expedite hardware or software application requests for quotation in a user friendly manner and leads a user through each step in detail and provides a smart context sensitive search that makes it easy for the user to search for desired data fields in a database for incorporation in a quotation. The smart search also is adaptively automatically customized based on previous user requirements derived from previous searches and automatically provides candidate search results.

Figure 1:
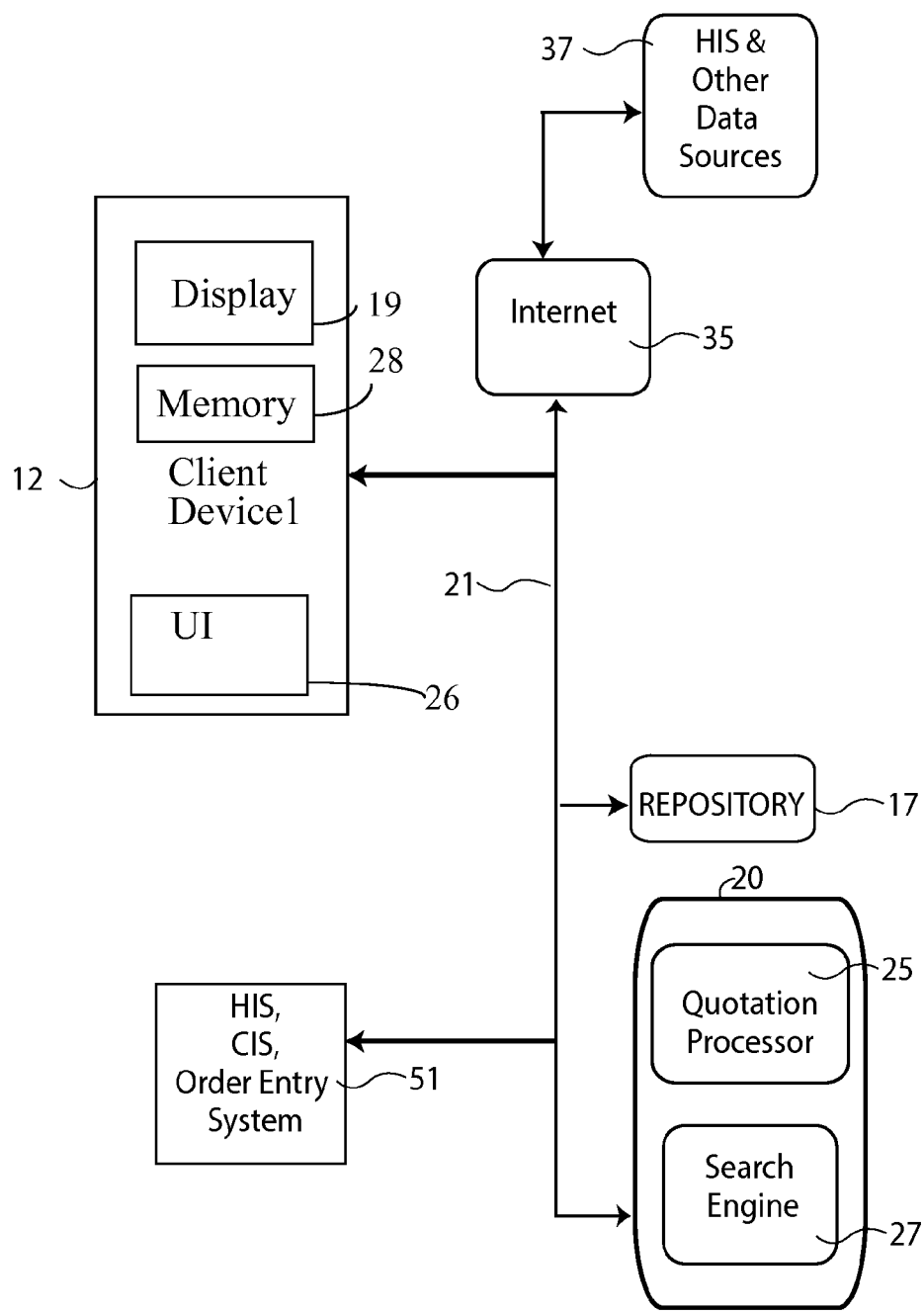
FIG. 1 shows a system for generating a request for quotation for healthcare information system resources from a vendor, according to invention principles.

FIG. 1 shows system 10 for generating a request for quotation for healthcare information system resources to be provided by a vendor. System 10 includes one or more processing devices on network 21 (e.g., workstations, computers or portable devices such as notebooks, Personal Digital Assistants, phones) 12 that individually include a user interface 26 enabling user interaction with a Graphical User Interface (GUI) and display 19 supporting a graphical user interface (GUI). System 10 also includes at least one repository 17, server 20 and HIS 51 (including admission, discharge and transfer (ADT), clinical information, order entry and other applications) intercommunicating via network 21. Server 20 includes quotation generator 25 and search engine 27. Server 20 communicates with data sources 37 via network 21 and Internet 35 or via Internet 35 directly (connection not shown to preserve drawing clarity).

At least one repository of information 17 includes, a template quotation format and multiple different quotation related data fields associated with multiple different healthcare information system resources. Context sensitive search engine 27 receives user entered text data associated with a desired healthcare information system resource and searches repository 17 to identify multiple different quotation related data fields associated with a healthcare information system resource in response to the entered text data. Quotation generator 25 populates a template quotation request form derived from the at least one repository with the identified multiple different quotation related data fields associated with a healthcare information system resource in response to the entered text data. Context sensitive search engine 27 identifies a desired healthcare information system resource from multiple different healthcare information system resources in response to user entered text data.

Figure 2:
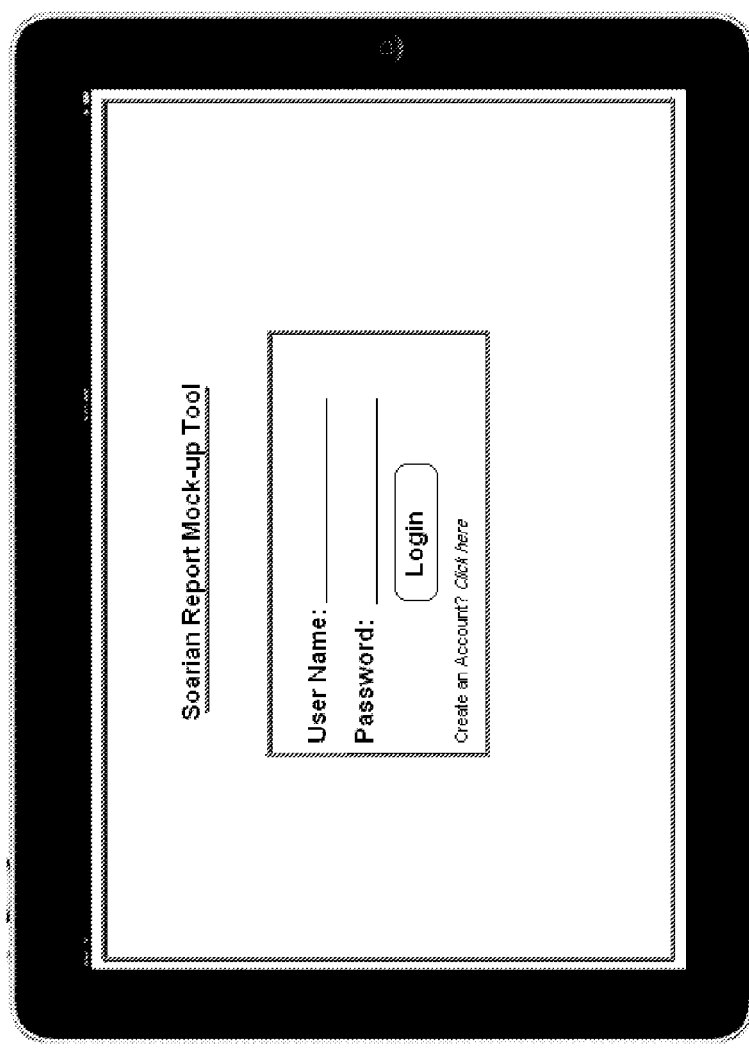
FIG. 2 shows a system login display image.
Figure 3:
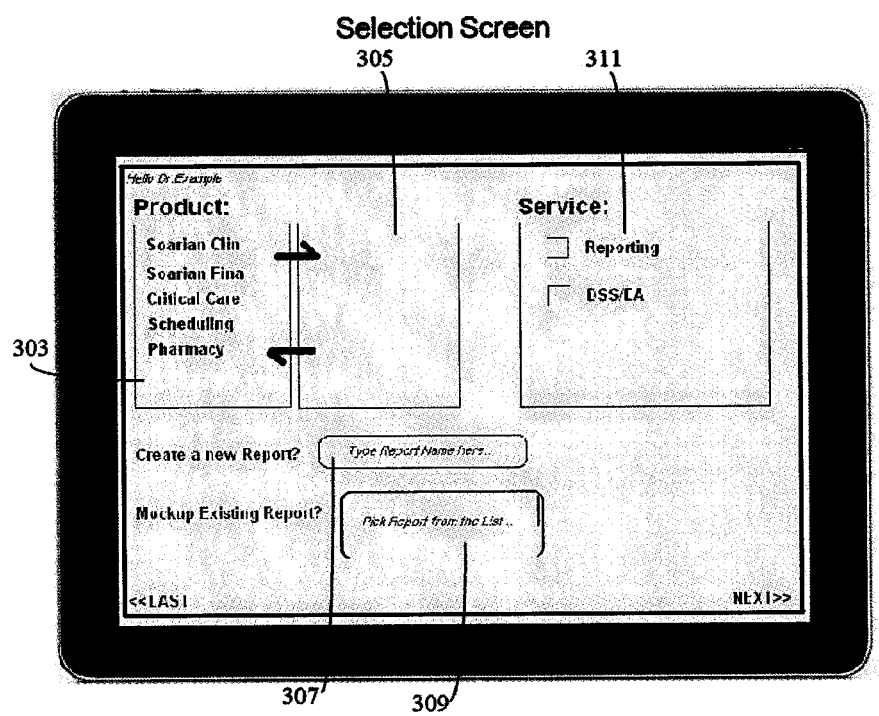
FIG. 3 shows an HIS application selection display image enabling selection of applications for quotation, according to invention principles.

FIG. 2 shows a system login display image enabling user access to the quotation preparation system in response to entry of a userid and password. FIG. 3 shows an HIS application selection display image enabling selection of applications for quotation. A user selects one or more executable applications for quotation in window area 303 and moves the selected applications into selected application area 305 in response to a drag and drop action or button activation. A user is also able to select generation of a new quotation request via element 307 or a user is able to choose modification of an existing quotation selectable from a list in response to activation of item 309. A type of service, such as a quotation request or upgrade request, is selected in window area 311.

Figure 4:
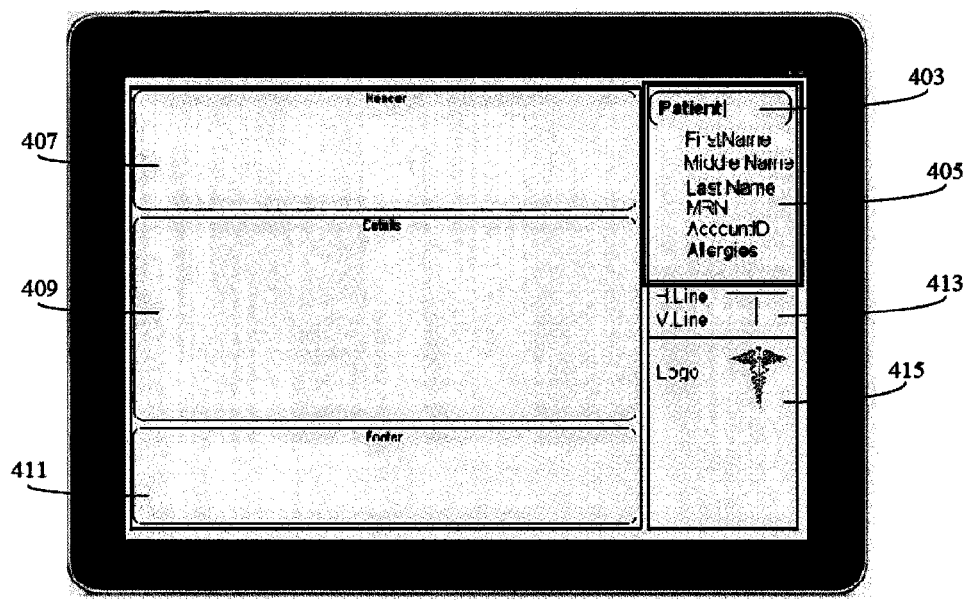
FIG. 4 shows an HIS application quotation display image populated by data fields in response to a user initiated search and drag and drop selection or by typing text, according to invention principles.

FIG. 4 shows an HIS application quotation display image to be populated by data fields in response to a user initiated search and drag and drop selection or by typing text. A user enters text in search box 403 and search engine 27 automatically searches for matching medical report data items in repository 17 and searches for matching medical report data items at remote sources 37 (via Internet 35) as search text is entered. A search is performed based on text string matching and associated category items. For example entry of the word "patient" brings up a category of items associated with a patient including name data fields, MRN (medical record number), account and allergies data fields, for example. Search result items are displayed for user selection in area 405 and user drag and drop into quotation request header, detail and footer sections 407, 409 and 411, respectively. A user is also provided with report layout features including lines and a logo and other layout supporting feature in areas 413 and 415 for selection and drag and drop incorporation in the report.

Figure 5:
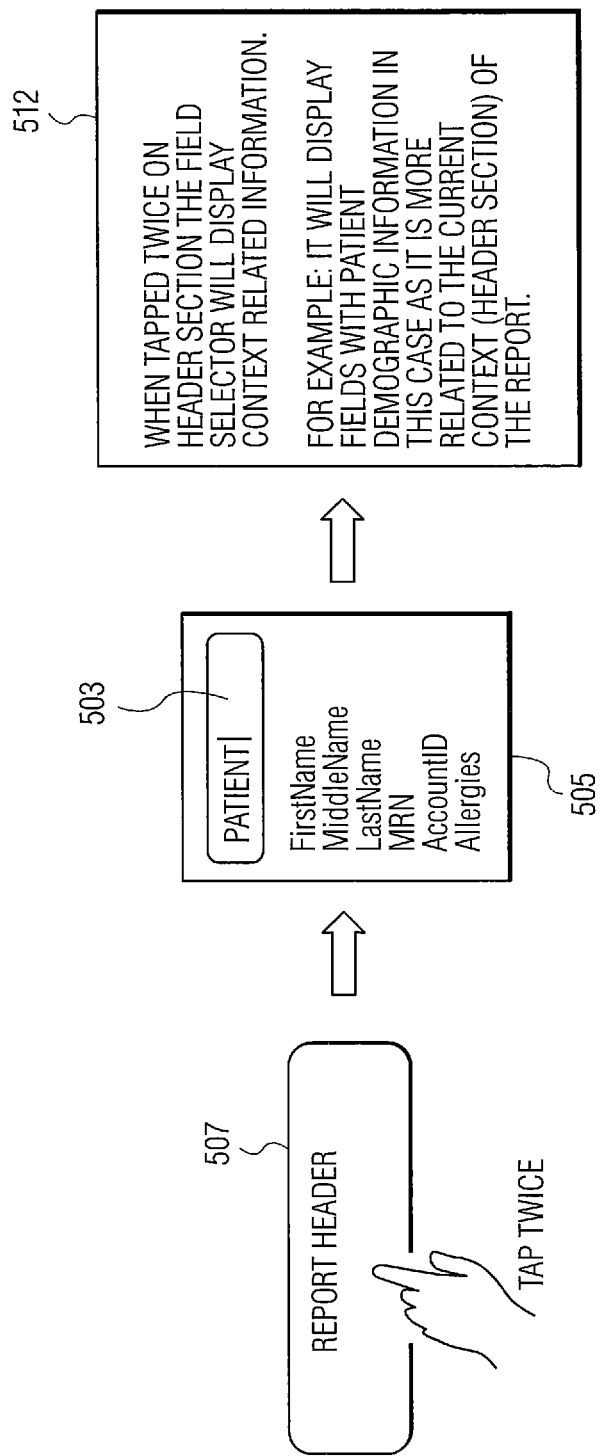
FIG. 5 shows illustration of a process for context sensitive item selection and request for quotation population, according to invention principles.

FIG. 5 shows illustration of a process for context sensitive item selection and request for quotation population. A user is also able to show candidate data fields that may be selected for a header, detail and footer section based on context comprising current content of the quotation report and/or the search result. In response to a user selecting header area 507 twice (e.g. via double touchscreen tap or mouse double click) candidate data fields are presented for a quotation report. For example, if a current search term "patient" is entered in search box 503, candidate patient related data fields include the name data fields, MRN, account and allergies data fields, shown in area 505 are presented for selection for header 507. If there is no current search term entered in search box 503, quotation processor 25 shows demographic and administrative data fields (including name, MRN, account, allergies, age, weight, height, gender, pregnancy status, admission, discharge transfer status, data fields, for example) that are related to current report context including content and type of report selected. The candidate data fields are available for selection and automatic incorporation in the selected portion of the report in response to user command.

Figure 6:
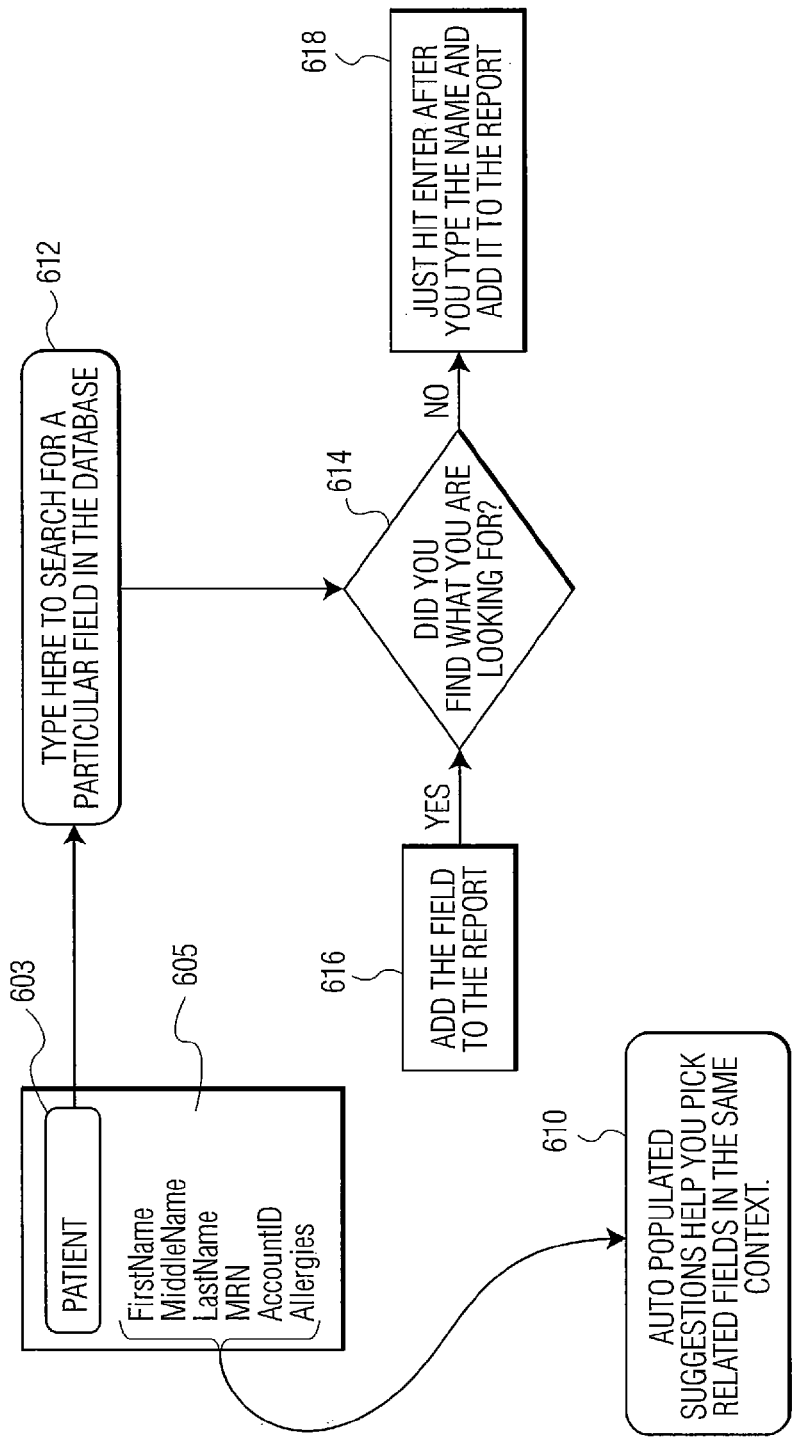
FIG. 6 shows a process for user context sensitive item selection and incorporation in a request for quotation, according to invention principles.

FIG. 6 shows a process for user context sensitive item selection and incorporation in a request for quotation. A user in step 612 enters text in search box 603 to search for a particular data field and in response to determining in step 614 that the desired data field is found, a user adds the data field to the report e.g. by drag and drop operation in step 616. In response to determining in step 614 that the desired data field is not found, a user types text comprising the desired data field label in step 618 and the labeled desired data field is incorporated into the report. The search related auto-populated candidate data fields 605 facilitate user selection of data fields for incorporation into the report in the same context, in step 610.

Figure 7:
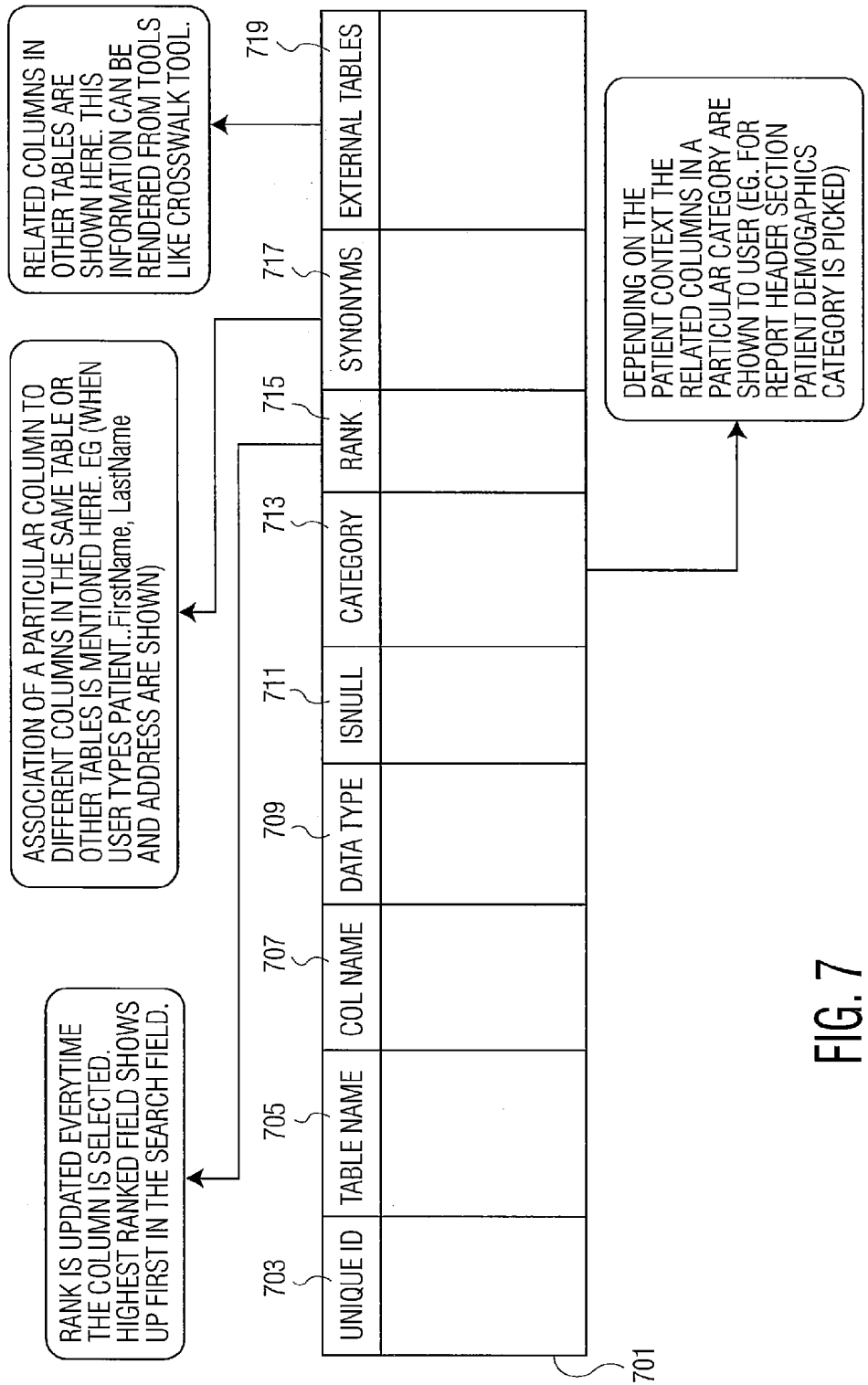
FIG. 7 shows a table for an individual data item used by the system for generating a request for quotation, according to invention principles.

FIG. 7 shows a table for an individual data field stored and usable by system 10 (FIG. 1) for generating a request for quotation. An individual data field is stored in a database in repository 17 in association with multiple different parameters supporting data field identification and incorporation into a request for quotation report. In one embodiment a tabular type association is used, but other types of database association are usable as readily appreciated by one of ordinary skill in the art. An individual data field and associated label has one or more of, a unique identifier (703) and table (701) having a table name (705) and presentation column (707) in a quotation request report. Data presented in a data field has a data type (709) and null characteristic (711) indicating the maximum length of data in the data field is completed with null data, for example. Table 701 further associates the individual data field with a category 713 indicating related data fields that are presented to a user in response to entry of text identifying the data field in a search box (e.g. box 403 FIG. 4). For example, in response to entry of "patient" in a search box, demographics data fields are shown in window area 405 (FIG. 4). Rank 715 indicates a priority in which data fields are displayed to a user in response to a search by search engine 27 (FIG. 1) and rank is updated in response to selection of a candidate data field resulting from a search. Synonyms 717 lists data fields directly related to, or that are synonyms of, a data field in the search box. For example, in response to entry of "patient" in search box 403, synonym 717 for the patient data field lists patient name and address. External tables 719 shows links to columns of tables of other data fields and the other data fields themselves as well as their category and synonym related data fields. The system automatically searches the other tables for data fields linked to a desired data field using external table 719 links and presents the data fields as search results in area 405 (FIG. 4), for example.

Figure 8:
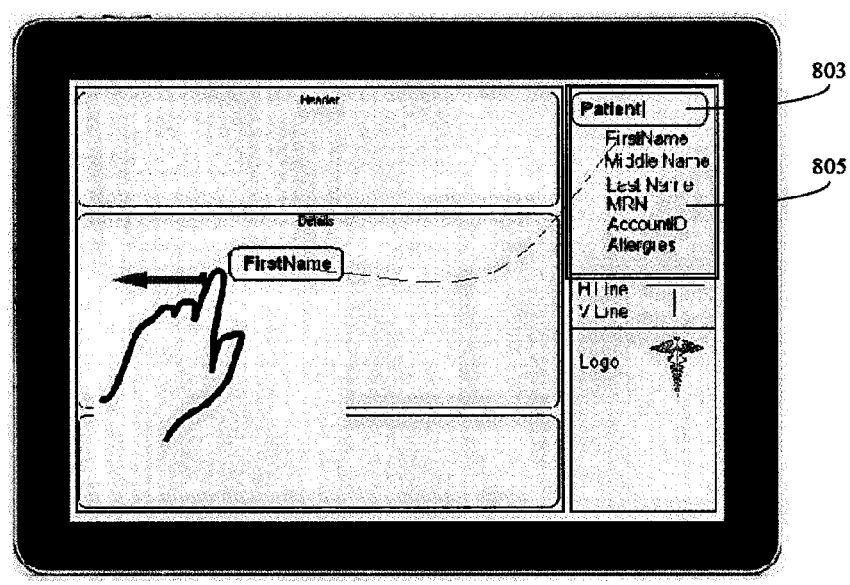
FIG. 8 shows an HIS application quotation request display image enabling user population of data fields, according to invention principles.

FIG. 8 shows an HIS application quotation request display image enabling user population of data fields. A user performs a drag and drop operation of a data field (e.g. Firstname) from window area 805 into a details section of a quotation request form following a data field search in response to entry of a data field in search box 803. The drag and drop operation is performed by mouse or touch using a touchscreen, for example.

Figure 9:
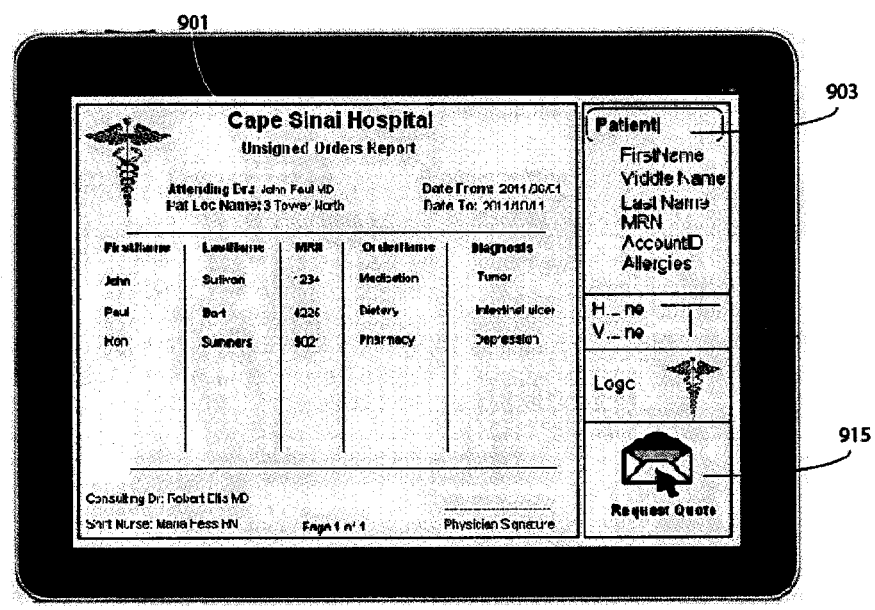
FIG. 9 shows a display image created by a user using data fields derived by a search and placed by the user, according to invention principles.

FIG. 9 shows display image 901 created by a user using data fields derived by a search via search box 903 and placed by the user via a drag and drop operation. Specifically, image 901 comprises an unsigned orders report showing orders placed for a medication, a dietary service and pharmacy order, for example, that a user wishes to be provided by a healthcare information system. A user initiates a request for quotation for an executable application providing the unsigned orders report and associated functions, by selecting button 915. In response to user selection of button 915, system 10 (FIG. 1) sends user created image 901 and a message requesting a quotation for an executable application providing the unsigned orders report and associated executable application functions to a hospital information system vendor. The message may request provision of a new executable application or modification of an existing application if an application is already possessed by a user that is related to the requested image and associated function.

System 10 (FIG. 1) advantageously reduces the number of steps involved in requesting a quotation for an executable application function and associated user interface comprising one or more display images and reduces the time duration of an executable application quoting process. The system facilitates finding desired data fields in a database during preparation of a request for quotation of different executable application functions and reducing quotation generation time. The system in one embodiment is integrated with other systems to extract information that a user needs. The ease of use of the system saves time, effort and money in requesting resources from a vendor and eliminates dependency on an external technical resource to request a quote. The system enables a user to request online quotations for executable application functions and associated user interface images with minimal need for customization. A data dictionary is updated with fields for a new product performable with use of Ad-hoc SQL queries.

The system employs an intuitive user interface and search feature for finding different data fields in a database for advantageously generating a request for quotation. In one embodiment, the request for quotation includes at least one user created user interface display image. The system is usable by workers for promoting and selling services or features associated with a new or existing executable application and by customers in requesting a quotation and submitting questions about a particular data field. The system is integrated with other systems and data sources facilitating search for similar data field names in other databases that are equivalent of a desired data field.

Figure 10:
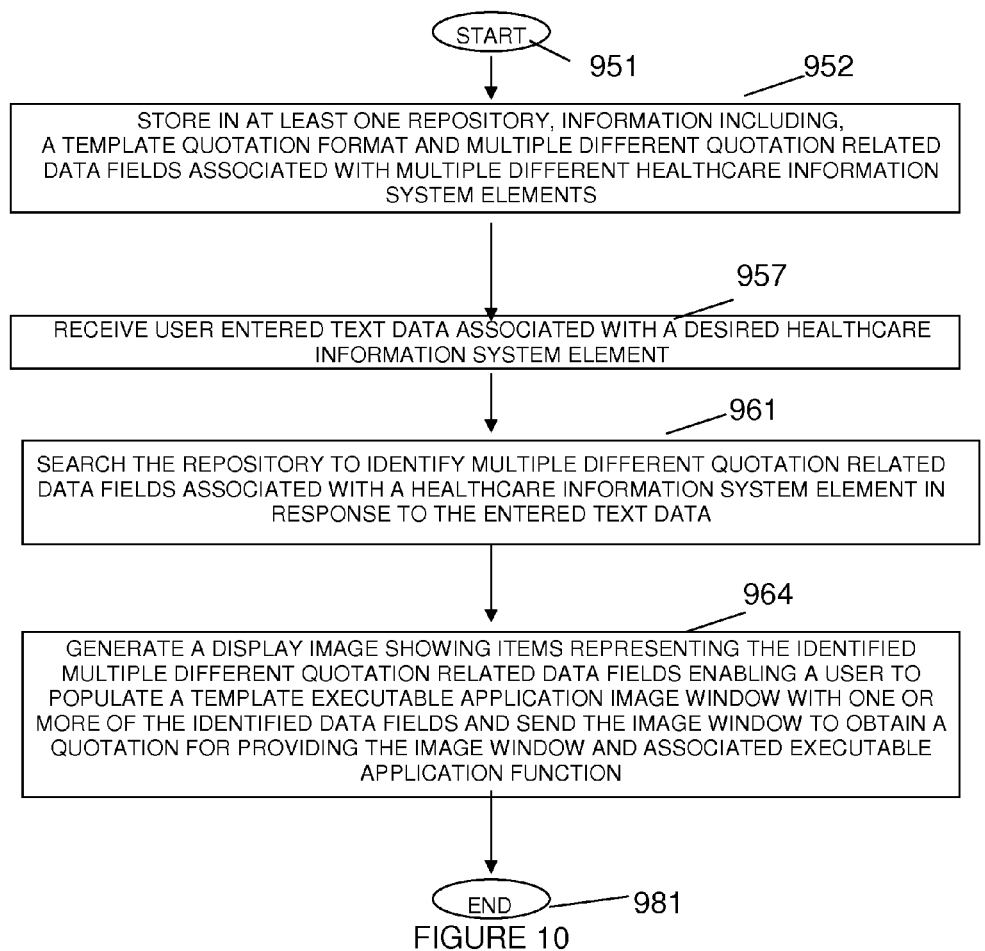
FIG. 10 shows a flowchart of a process performed by the system for generating a request for quotation for healthcare information system resources from a vendor, according to invention principles.

FIG. 10 shows a flowchart of a process performed by system 10 (FIG. 1) for generating a request for quotation for healthcare information system resources and executable application functions from a vendor. In step 952 following the start at step 951, quotation processor 25 stores in at least one repository 17, information including, a template quotation format and multiple different quotation related data fields associated with multiple different healthcare information system elements and resources. The at least one repository of information associates an individual data field with a category of data fields related to the individual data field and with a synonym of the individual data field and with other different data fields. In step 957, context sensitive search engine 27 receives user entered text data associated with a desired healthcare information system element or system resource and in step 961 searches repository 17 to identify multiple different quotation related data fields associated with a healthcare information system element or system resource in response to the entered text data.

A healthcare information system element comprises at least one of, (a) healthcare information system resource and (b) healthcare information system information item. The context sensitive search engine identifies a desired healthcare information system element from multiple different healthcare information system elements in response to user entered text data. Specifically, in response to the entered text data, the context sensitive search engine automatically finds the individual data field, the category of data fields, the synonym of the individual data field and other different data fields. In response to the entered text data comprising the word patient, for example, the context sensitive search engine finds data fields comprising patient name and address and retrieves demographics data fields for presentation in the display image.

Quotation generator 25 in step 964 automatically populates a template quotation request form or report form derived from the at least one repository with the identified plurality of different quotation related data fields associated with a healthcare information system resource in response to the entered text data. Quotation processor 25 in step 964 also generates a display image showing items representing the identified multiple different quotation related data fields enabling a user to populate a template executable application image window with one or more of the identified data fields and to send the image window to obtain a quotation for providing the image window and associated executable application function. The display image shows the items representing the identified plurality of different quotation related data fields comprising search results adjacent to a search term data entry box for receiving user entered text data. The identified multiple different quotation related data fields are ranked in list order in response to a predetermined likelihood a data field is a desired data field associated with the entered text data and the ranking intermittently is updated in response to selection of a candidate data field resulting from a search. The display image enables a user to populate the template executable application image window by using a drag and drop operation for moving at least one of the identified data fields into the image window. Further, the display image shows graphic items representing at least one of, (a) a horizontal line, (b) a vertical line and (c) a logo and enabling a user to populate the template executable application image window with one or more of the graphic items. The process of FIG. 10 terminates at step 981.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command An activity (including a step) performed automatically is performed in response to executable instruction or device operation without user direct initiation of the activity.

The system and processes of FIGS. 1-10 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system enables a user to request online quotations for an executable application, addition or function and associated user interface images. Further, the processes and applications may, in alternative embodiments, be located on one or more (e.g., distributed) processing devices on a network linking the units of FIG. 1. Any of the functions and steps provided in FIGS. 1-10 may be implemented in hardware, software or a combination of both. No claim element herein is to be construed under the provisions of 35 U.S.C. 112, sixth paragraph, unless the element is expressly recited using the phrase "means for."

What is claimed is:

1. A system for generating a request for quotation for healthcare information system resources from a vendor, comprising:
   at least one repository hardware of information including,
      a template quotation format; and
      a plurality of different quotation related data fields associated with a plurality of different healthcare information system elements to be provided by at least one healthcare information system vendor; and
   a server hardware including,
      a context sensitive search engine for receiving user entered text data associated with a desired healthcare information system element and for searching said repository to identify a plurality of different quotation related data fields associated with a healthcare information system element in response to said entered text data, and
      a quotation generator for generating a display image showing items representing the identified plurality of different quotation related data fields ranked in list order in response to a predetermined likelihood a data field is a desired data field associated with said entered text data, wherein the rank is updated in response to selection of a candidate data field resulting from a search, said display image enabling a user to populate a template executable application image window with one or more of the identified data fields and to submit, to the healthcare information system vendor, the image window with a message requesting a quotation for providing the image window and associated executable application function.

2. The system according to claim 1, wherein said context sensitive search engine identifies a desired healthcare information system element from a plurality of different healthcare information system elements in response to user entered text data.

3. The system according to claim 1, wherein the healthcare information system elements to be provided by at least one healthcare information system vendor comprise at least one medication, dietary service or pharmacy order.

4. The system according to claim 1, wherein said display image enables a user to populate said template executable application image window by using a drag and drop operation for moving at least one of said identified data fields into said image window.

5. The system according to claim 1, wherein said display image shows said items representing the identified plurality of different quotation related data fields comprising search results adjacent to a search term data entry box for receiving user entered text data.

6. The system according to claim 1, wherein said display image shows graphic items representing at least one of, (a) a horizontal line, (b) a vertical line and (c) a logo and enabling a user to populate said template executable application image window with one or more of said graphic items.

7. The system according to claim 1, wherein said at least one repository of information associates an individual data field with a category of data fields related to said individual data field; and
   in response to said entered text data, said context sensitive search engine finds said individual data field and said category of data fields.

8. The system according to claim 1, wherein said at least one repository of information associates an individual data field with a synonym of said individual data field; and in response to said entered text data, said context sensitive search engine finds said synonym of said individual data field.

9. The system according to claim 8, wherein in response to said entered text data comprising the word patient, said context sensitive search engine finds data fields comprising patient name and address.

10. The system according to claim 1, wherein said at least one repository of information associates an individual data field with other different data fields; and said context sensitive search engine automatically finds said individual data field and other different data fields in response to said entered text data.

11. The system according to claim 1, wherein in response to said entered text data comprising the word patient, said context sensitive search engine retrieves demographics data fields for presentation in said display image.

12. The system according to claim 1, wherein said quotation generator automatically populates a template quotation request form derived from said at least one repository with the identified plurality of different quotation related data fields associated with a healthcare information system resource in response to said entered text data.

13. A method for generating a request for quotation for healthcare information system resources from a vendor, comprising the steps of:

retaining in at least one repository, information including,
a template quotation format; and
a plurality of different quotation related data fields associated with a plurality of different healthcare information system elements to be provided by at least one healthcare information system vendor;

receiving user entered text data associated with a desired healthcare information system element;

searching said repository to identify a plurality of different quotation related data fields associated with a healthcare information system element in response to said entered text data; and generating a display image showing items representing the identified plurality of different quotation related data fields ranked in list order in response to a predetermined likelihood a data field is a desired data field associated with said text data, wherein the rank is updated in response to selection of a candidate data field resulting from a search, said display image enabling a user to populate a template executable application image window with one or more of the identified data fields and send, to the healthcare information system vendor, the image window with a message requesting a quotation for providing the image window and associated executable application function.

14. The method according to claim 13, wherein said information associates an individual data field with a category of data fields related to said individual data field and including the step of, in response to said entered text data, finding said individual data field and said category of data fields.

15. A system for generating a report for requesting healthcare information system resources from a vendor, comprising:

at least one repository hardware of information including,
a template report format; and
a plurality of different resource related data fields associated with a plurality of different healthcare information system resources to be provided by at least one healthcare information system vendor; and a server hardware including,
a context sensitive search engine for receiving user entered text data associated with a desired healthcare information system resource and for searching said repository to identify a plurality of different resource related data fields associated with a healthcare information system resource in response to said entered text data, and
a quotation generator for populating a template report form derived from said at least one repository with the identified plurality of different quotation related data fields associated with a healthcare information system resource in response to said entered text data, wherein said data fields are ranked in list order in response to a predetermined likelihood a data field is a desired data field associated with said entered text data, and wherein the rank is updated in response to selection of a candidate data field resulting from a search.

16. The system according to claim 15, wherein said information associates an individual data field with a category of data fields related to said individual data field and including the step of,
in response to said entered text data, said context sensitive search engine finds said individual data field and said category of data fields.

\* \* \* \* \*